US007015189B2

(12) United States Patent
Narula et al.

(10) Patent No.: US 7,015,189 B2
(45) Date of Patent: Mar. 21, 2006

(54) OXIME METHYL ETHERS

(75) Inventors: Anubhav P. S. Narula, Hazlet, NJ (US); Rajamony Mahesh, Chennai (IN); Manfred Pawlak, Princeton, NJ (US); Patrick M. Merritt, Laurence Harbour, NJ (US); Clint Dee Winton Brooks, Sea Bright, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 428 days.

(21) Appl. No.: 10/231,690

(22) Filed: Aug. 29, 2002

(65) Prior Publication Data

US 2004/0043916 A1 Mar. 4, 2004

(51) Int. Cl.
*A61K 7/46* (2006.01)

(52) U.S. Cl. ............................ 512/25; 512/8; 512/11; 512/12; 512/20; 568/579; 568/583; 568/626

(58) Field of Classification Search .................... 512/8, 512/11, 12, 20, 25; 568/579, 583, 626; 564/254, 564/265

See application file for complete search history.

(56) References Cited

U.S. PATENT DOCUMENTS

| | | | | |
|---|---|---|---|---|
| 4,388,464 | A * | 6/1983 | Kristinsson et al. | ........ 548/136 |
| 4,534,891 | A | 8/1985 | Boden et al. | |
| 4,985,402 | A | 1/1991 | Narula et al. | |
| 4,990,494 | A | 2/1991 | Narula et al. | |
| 5,143,899 | A | 9/1992 | Narula et al. | |
| 5,179,222 | A | 1/1993 | Narula et al. | |
| 5,236,897 | A | 8/1993 | Narula et al. | |
| 5,300,488 | A | 4/1994 | Narula et al. | |
| 5,321,144 | A | 6/1994 | Narula et al. | |
| 6,924,263 | B1 | 8/2005 | Narula et al. | |

FOREIGN PATENT DOCUMENTS

EP 0 672 746 A1 9/1995

* cited by examiner

*Primary Examiner*—Monique T. Cole
(74) *Attorney, Agent, or Firm*—Joseph F. Leightner; Alexander Migirov

(57) ABSTRACT

The use of various novel oxime ethers are described as fragrance chemicals. These chemicals are suitable for use in creating fragrance, and scents in items such as perfumes, colognes and personal care products is disclosed.

15 Claims, No Drawings

OXIME METHYL ETHERS

FIELD OF THE INVENTION

The use of oxime methyl ethers is disclosed as fragrance chemicals suitable for incorporation in fine fragrances, cosmetics, toiletries and related applications.

BACKGROUND OF THE INVENTION

There is an ongoing need in the fragrance industry to provide new chemicals to give perfumers and other persons ability to create new fragrances for perfumes, colognes and personal care products.

One class of compounds that have been found to be particularly useful as fragrance chemicals are oxime ethers, more specifically propionitrile and propiohydroxyamine derivatives described in U.S. Pat. Nos. 4,985,402; 5,143,899; 5,179,222; 5,236,897 5,300,488; and 5,321,144; the contents hereby incorporated by reference as if set forth in its entirety; and European Patent Application 672,746.

Despite these disclosures there is an ongoing need to provide new fragrance chemicals in order to allow perfumers to create new fragrances and scents.

SUMMARY OF THE INVENTION

The present invention is directed to the discovery of novel compounds and the use of these compounds as fragrance chemicals to enhance fragrance in perfumes, toilet waters, colognes, personal products and the like.

In a first embodiment of the invention we have discovered the following novel compounds of the formula set forth below:

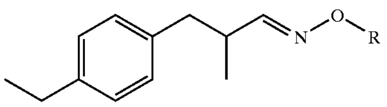

R=Me, Et, Allyl, Methylallyl, Cyclopentyl;

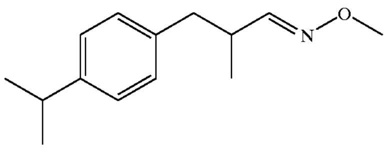

;

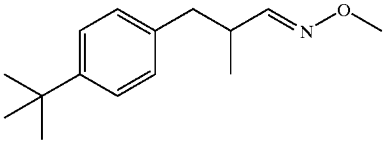

; and

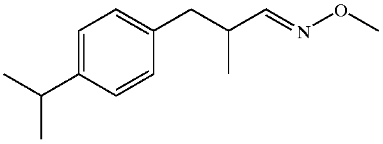

.

In a second embodiment, the present invention is a method for enhancing a perfume by incorporating an olfactory acceptable amount of compounds of the formula set forth above. The above materials can also be incorporated into fragrance formulations to provide unique fragrances.

These and other embodiments of the present invention will be apparent by reading the following specification.

DETAILED DESCRIPTION OF THE INVENTION

The present invention is directed to the novel compound and the use of these compounds in fragrance formulations.

We have discovered that the above described oxime methyl ethers compounds have a distinctive floral odor with some metallic notes that are well suited for use as a fragrance chemical.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; and musk; flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The novel compounds of the present invention are provided by the following general reaction sequence. Suitable starting material are compounds set forth in U.S. Pat. No. 4,990,494 the contents of which is incorporated by reference. The compounds are prepared by the following general reaction sequence. An appropriate size reaction flask equipped with a mechanical stirrer, condenser, addition funnel, and a temperature measurement thermocouple, is first charged with a given aldehyde and a suitable solvent such as ethylbenzene, toluene, and xylene at room temperature. To this is added an aqueous solution of hydroxylamine sulphate followed by a slow addition of 50% aqueous sodium hydroxide until basic and while maintaining the temperature below 40 degrees. The mixture is aged for 1 hour. The reaction mass is washed with brine, 10% aqueous solution, which gives an oxime that is distilled before use. These oximes were converted to oxime ethers using sodium hydride and appropriate alkylating agent, see the following experimental text for more specific examples.

The following are provided as specific embodiments of the present invention. Other modifications of this invention will be readily apparent to those skilled in the art, without departing from the scope of this invention. As used herein all percentages are weight percent. IFF as used in the examples is understood to mean International Flavors & Fragrances Inc., DPG is understood to mean dipropylene glycol, DEP is understood to mean diethylphthalate. In the formulae, Me is understood to be a methyl group and Et is understood to be an ethyl group.

EXAMPLE 1

Preparation of (1E)-1-aza-1-ethoxy-4-(4-ethylphenyl)-3-3-diemethyl-3,3-dimethyl but-1-ene To a dry 2 liter multi-neck round bottom flask fitted with an air stirrer, nitrogen inlet condenser and an addition funnel, 22 grams of NaH (supplied by Fluka as a 60% dispersion in oil) was added. The flask was maintained at a constant temperature of 20° C. via a water bath. The NaH was washed with three 30 milliliter doses of petroleum ether and the washings were discarded. Tetrahydrofuran (THF) was added to the flask (250 ml), followed by 95 grams of floralozone oxime, as was described in U.S. Pat. No. 4,990,494, in 250 ml of THF over a two hour period while being vigorously stirred. After the addition was complete, 86 grams of methyl iodide (SpectroChem) in 250 ml of THF is slowly added over two hours. The resulting mixture was stirred at room temperature until the oxime was consumed.

The resulting thick white mass was cooled to 10° C. and then 100 ml of water is added under vigorous stirring. The resulting mass was transferred to a 5 liter separatory funnel. 500 ml of solvent ether was added to the reaction product and the organics were washed with three 250 ml water until the aqueous layer was pH neutral. The organic layer was dried over sodium sulfate and the solvent is removed under reduced pressure to provide 90 grams of the crude product.

NMR data 1.1–1.3 ppm (ms, 12H), 2.6–2.78 ppm(m, 4H), 4.1 ppm (m, 2H), 7–7.34 ppm (m, 5H).

The fragrance of this compound was evaluated and was described as green, floral and having pettit green notes.

EXAMPLE 2

Preparation of (1E)-1-aza-4-(4-ethylphenyl)-1-methoxy-3,3-dimethylbut-1-ene

To a dry 5 liter multi-neck round bottom flask fitted with air stirrer, nitrogen inlet, condenser, and addition funnel 96 grams of NaH was added. The vessel was maintained at 20° C. via a water bath. The NaH was washed with three 75 milliliter doses of petroleum ether and the washings were discarded. Tetrahydrofuran (THF) was added to the flask (1000 ml), followed by 405 grams of floralozone oxime in 8000 ml of THF over a three hour period while being vigorously stirred. After the addition was complete, 341 grams of methyl iodide (SpectroChem) in 250 ml of THF was slowly added over ten hours. The resulting mixture was stirred at room temperature until the oxime was consumed.

The resulting thick white mass was cooled to 10° C. and then 500 ml of water was added under vigorous stirring. The resulting mass was transferred to a 5 liter separatory funnel. 1000 ml of solvent ether was added to the reaction product and the organics were washed with three 1000 ml water until the aqueous layer was pH neutral. The organic layer was dried over sodium sulfate and the solvent was removed under reduced pressure to provide 400 grams of the crude product.

NMR data 1.1–1.25 ppm (ms, 12H), 2.5–2.75 ppm (m, 4H), 3.8 ppm (s, 3H), 7–7.3 ppm (m, 5H).

The fragrance of this compound was evaluated and was described as strong green, floral fragrance with pettit green notes.

EXAMPLE 3

Preparation of 1-(hydroxyimino)-3-[4-(methylethyl)phenyl]propane

Apparatus similar to that of Examples 1 and 2 was used.

Water (1200 grams) and hydroxylamine sulfate (354 grams, Aldrich) was charged to the flask under constant agitation until clear. Cyclemax (available from IFF, 33 grams) was added to the flask at 33° C. over a 5 minute period. Caustic (50 weight %) was added to the flask over 30 minutes. Toluene (970 grams) was added and the flask contents were transferred to a separatory funnel and the contents were allowed to separate. The organic layer was washed with a 1000 ml water wash, a 1000 ml of acetic acid (5% by weight) and two water washes. The organic layer was heated with steam to remove any residual solvent and the resulting crystals were allowed to dry. A 97% yield based on the aldehyde charge was obtained.

NMR data 1.25 ppm (d, 6H), 2.65–2.93 ppm (m, 5H), 6.75 ppm (m, 1H), 7.2 ppm (m, 4H), 8.2 ppm (bs, 1H).

The fragrance of this compound was evaluated and was described as chemical, muguet like.

EXAMPLE 4

Preparation of (1E)-1-aza-1-methoxy-4-(4-methylethyl)phenyl but-1-ene

The apparatus of Example 1 was used and 1000 ml of THF was charged. NaH (60.3 g) was charged under a nitrogen blanket and with constant agitation. THF (500 ml) and 240 grams of cyclemax oxime (IFF) was mixed separately in a 1000 ml Erlenmeyer flask. The cyclemax oxime/THF solution was charged to the reaction flask over 3 hours. After the addition was complete the contents were heated to 40° C. for 30 minutes. The contents were then cooled to 20° C. for 30 minutes. The contents were further cooled to 20° C. and methyl iodide (214 grams, Aldrich) was added over 3 hours. The contents were cooled to 0° C. and 500 mls of water was added over 15 minutes. The contents of the flask were moved to a 12 liter separatory funnel and 1 liter of hexane and 1 liter of brine was added. The resulting aqueous layer was removed. The organic layer was washed with a 2000 ml water wash and three 2000 ml brine washes.

The above process provided about 1025 grams of product.

NMR data 1.25 ppm (2s, 6H), 2.5–2.9 ppm (m, 3H), 3.8 ppm (s, 3H), 6.7 ppm (m, 1H), 7.14–7.4 ppm (m, 4H).

The fragrance of this compound was evaluated and was described as similar to LILIAL (Givaudan), muguet, and hydroxycitronellol.

EXAMPLE 5

Preparation of (1E)-1-aza-4-(4-ethylphenyl)-3,3-dimethyl-1-prop-2-enyloxy-but-1-ene To a dry 5 liter multi-neck round bottom flask fitted with an air stirrer, nitrogen inlet condenser and an addition funnel, 36 grams of NaH (supplied by Fluka as a 60% dispersion in oil) was added. The flask was maintained at a constant temperature of 20° C. via a water bath. The NaH was washed with three 50 milliliter doses of petroleum ether and the washings were discarded. Tetrahydrofuran (THF) was added to the flask (250 ml), followed by 153 grams of floralozene oxime in 250 ml of THF over a three hour period while being vigorously stirred. After the addition was complete, 98 grams of allyl bromide in 200 ml of THF was slowly added over two hours. The resulting mixture is stirred at room temperature until the oxime was consumed.

The resulting thick white mass was cooled to 10° C. and then 200 ml of water was added under vigorous stirring. The resulting mass was transferred to a 5 liter separatory funnel. 500 ml of solvent ether was added to the reaction product and the organics were washed with three 250 ml of water until the aqueous layer was pH neutral. The organic layer was dried over sodium sulfate and the solvent was removed under reduced pressure to provide 160 grams of the crude product.

NMR data 1.1–1.25 ppm (ms, 9H), 2.6–2.78 ppm (m, 4H), 4.5 ppm (m, 2H), 5.15–5.3 (q, 1H), 5.9–6 ppm (m, 1H), 7–7.4 ppm (m, 5H).

The fragrance of this compound was evaluated and was described as floral.

EXAMPLE 6

Preparation of (1E)-1-aza-4-(4-ethylphenyl)-3,3-dimethyl-1-(2-methylprop-2-enyloxy) but-1-ene To a dry 5 liter multi-neck round bottom flask fitted with an air stirrer, nitrogen inlet condenser and an addition funnel, 46 grams of NaH (supplied by Fluka as a 60% dispersion in oil) was added. The flask was maintained at a constant temperature of 20° C. via a water bath. The NaH was washed with three 50 milliliter doses of petroleum ether and the washings were discarded. Tetrahydrofuran (THF) was added to the flask (250 ml), followed by 205 grams of floralozone oxime in 400 ml of THF over a three hour period while being vigorously stirred. After the addition was completed, 104 grams of methallyl chloride in 250 ml of THF was slowly added over two hours. The resulting mixture was stirred at room temperature. After about 12 hours of stirring, the flask was cooled to about 15° C. and 600 grams of sodium iodide was slowly added over two hours. The resultant mixture was stirred for about seven days until the starting oxime was consumed.

The resulting thick mass was cooled to 10° C. and then 500 ml of water was added under vigorous stirring. The resulting mass was transferred to a 10 liter separatory funnel. 1500 ml of solvent ether was added to the reaction product and the organics were washed with three 1000 ml washes of water until the aqueous layer was pH neutral. The organic layer was dried over sodium sulfate and the solvent was removed under reduced pressure to provide 180 grams of the crude product.

NMR data 1.1–1.3 ppm (ms, 9H), 1.8 ppm (s, 3H), 2.65–2.8 ppm (m, 4H), 4.5 ppm (s, 2H), 5 ppm (d, 2H), 7.45 ppm (m, 5H).

The fragrance of this compound was evaluated and was described as floral.

EXAMPLE 7

Preparation of benzenepropanal-4-ethyl-alpha,alpha-dimethyl-, O-cyclopentyloxime To a dry 5 liter multi-neck round bottom flask fitted with an air stirrer, nitrogen inlet condenser and an addition funnel, 46 grams of NaH (supplied by Fluka as a 60% dispersion in oil) was added. The flask was maintained at a constant temperature of 20° C. via a water bath. The NaH was washed with three 50 milliliter doses of petroleum ether and the washings were discarded. Tetrahydrofuran (THF) was added to the flask (250 ml), followed by 205 grams of floralozone oxime in 400 ml of THF over a three hour period while being vigorously stirred. After the addition was completed, 170 grams of cyclopentyl bromide in 250 ml of THF was slowly added over two hours. The resulting mixture was stirred at room temperature. After about 12 hours of stirring, the flask was cooled to about 15° C. and 150 grams of sodium iodide was slowly added over a period of 15 minutes while stirring. Another three installments of 450 grams of sodium iodide were added once every 24 hours. At this point, the product was reacted to provide a yield of about 64%, the remainder material being primarily starting material and the work-up is started.

The resulting thick mass was cooled to 10° C. and then 250 ml of water was added under vigorous stirring. The resulting mass was transferred to a 10 liter separatory funnel. 1500 ml of solvent ether was added to the reaction product and the organics were washed with three 1000 ml of water until the aqueous layer was pH neutral. The organic layer was dried over sodium sulfate and the solvent was removed under reduced pressure to provide 240 grams of the crude product.

NMR data 1.15–1.28 ppm (sm, 14H), 1.5–1.7 ppm (m, 12H), 2.58–2.78 ppm (m, 6H), 4.6 ppm (m, 1H), 7–7.3 ppm (m, 5H).

The fragrance of this compound was evaluated and was described as floral.

EXAMPLE 8

Preparation of (1E)-1-aza-1-methoxy-3-methyl-4-[4-(methylethyl)phenyl]but-1-ene To a dry 5 liter multi-neck round bottom flask fitted with an air stirrer, nitrogen inlet condenser and an addition funnel, 120 grams of NaH (supplied by Fluka as a 60% dispersion in oil) was added. The flask was maintained at a constant temperature of 20° C. via a water bath. The NaH was washed with three 150 milliliter doses of petroleum ether and the washings were discarded. Tetrahydrofuran (THF) was added to the flask (750 ml), followed by 500 grams of canthoxal oxime in 900 ml of THF over a three and a half hour period while being vigorously stirred. After the addition was complete, 426 grams of methyl iodide in 600 ml of THF was slowly added over three hours. The resulting mixture was stirred at room temperature overnight until the oxime was consumed.

The resulting thick white mass was cooled to 10° C. and then 500 ml of water was added under vigorous stirring. The resulting mass was transferred to a 10 liter separatory funnel. 1.5 Liters of solvent ether was added to the reaction product and the organics were washed with three 1 liters of water until the aqueous layer was pH neutral. The organic layer was dried over sodium sulfate and the solvent was removed under reduced pressure to provide 440 grams of the crude product.

NMR data 1.17 ppm (m, 3H), 2.5–2.8 ppm (m, 2H), 3.8 ppm (s, 6H), 6.8–7.35 ppm (m, 4H).

The fragrance of this compound was evaluated and was described as having a good, strong anethol, and floral notes.

EXAMPLE 9

Preparation of (1E)-1-aza-1-methoxy-3-methyl-4-[4-(methylethyl)phenyl]but-1-ene To a dry 5 liter multi-neck round bottom flask fitted with an air stirrer, nitrogen inlet condenser and an addition funnel, 96 grams of NaH (supplied by Fluka as a 60% dispersion in oil) is added. The flask is maintained at a constant temperature of 20° C. via a water bath. The NaH is washed with three 150 milliliter doses of petroleum ether and the washings are discarded. Tetrahydrofuran (THF) is added to the flask (1 liter), followed by 410 grams of cyclamal oxime in 800 ml of THF over a four hour period while being vigorously stirred. After the addition was complete, 340 grams of methyl iodide in 700 ml of THF was slowly added over three hours. The resulting mixture was stirred at room temperature overnight until the oxime was consumed.

The thick white mass was cooled to 10° C. and then 500 ml of water was added under vigorous stirring. The resulting mass was transferred to a 10 liter separatory funnel. 1.5 Liters of solvent ether was added to the reaction product and the organics were washed with three 1 liters of water until the aqueous layer was pH neutral. The organic layer was dried over sodium sulfate and the solvent was removed under reduced pressure to provide 400 grams of the crude product.

NMR data 1.0 ppm (d, 3H), 1.2 ppm (d, 6H), 2.5–2.9 ppm (m, 4H), 3.8 ppm (s, 3H), 6.5 (d, 1H), 7–7.3 ppm (m, 4H).

The fragrance of this compound was evaluated and described as methyl chavicol, coumarin, cherry blossom, ozoney and vanillin notes.

EXAMPLE 10

Preparation of benzenepropanal,4-(1,1,-dimethylethyl)-O-methyloxime

Water (700 ml) and hydroxylamine sulfate (169 gms, Aldrich) were charged to a 5 liter reactor, nitrogen feed, condenser, stirring apparatus, isopropyl alcohol bath and a temperature probe. Bourgenal (256 gms, source) was charged to the reactor over a period of 10 minutes. Caustic solution (50% solution, 185 grams) was added to the reactor over a period of 30 minutes while the bath was used to maintain the temperature below 35° C. Ethyl acetate (300 ml) was added to the reactor. The contents of the reactor were moved to a separatory funnel to remove the layers.

The organic layer was washed 3 times with a brine solution and distilled: BP=150 C at 3 mm Hg. The product yield was 86.5 percent based upon aldehyde charged.

NMR data 1.3 ppm (s, 9H), 2.45–2.8 ppm (m, 4H), 7.1–7.58 ppm (m, 5H).

The fragrance of this compound was evaluated and was described as sweet and having heliotropine notes.

EXAMPLE 11

Preparation of benzenepropanal, 4-(1,1-dimethylethyl)-O-methyloxime

Tetrahydrofuran (1000 grams) was charged to a 5 liter reactor, nitrogen feed, Claisen adapter, condenser, stirring apparatus, bubbler, and a temperature probe. NaH (71.3 gms, Aldrich) was charged to the reactor under nitrogen blanket with constant stirring over 10 minutes. Another 400 mls of THF was mixed with bourgeonal oxime (300 grams) in an Erlenmeyer flask. The bourgeonal oxime solution was added to the reaction flask over a 3 hour period. Hydrogen evolution was monitored with the bubbler. After all the NaH was finished reacting, methyl iodide (258 gms, Aldrich) was added over 3 hours. The reactor was cooled to −10° C. and 50 ml of water was added dropwise over an hour. The reactor contents were transferred to a separatory funnel and 500 ml of toluene and 500 ml of water was added. The organic layer was washed with successive washes of 1000 ml of water, 1000 ml of 2.5% acetic acid and two 1000 ml of water. The remaining material was filtered through CELITE (Johns-Manville Company)/sodium sulfate and distilled: BP=134° C. at 3.85 mm Hg. 720 grams of crude product gives a yield of about 20.2%.

NMR data 1.3 ppm (s, 9H), 2.45–3.0 ppm (m, 4H), 3.8 ppm (s, 3H), 7.1–7.4 ppm (m, 5H).

The fragrance of this compound was evaluated and was described as being floral, minty and cooling.

EXAMPLE 12

Preparation of benezenepropanal, 4-(1,1-dimethyl ethyl)-alpha-methyl-, O-methyloxime 1,2-dimethoxy ethane (850 grams, Fluka) was charged to a 5 liter reactor, nitrogen feed, Claisen adapter, condenser, stirring apparatus, bubbler, and a temperature probe. NaH (100 grams, Aldrich) was added under nitrogen blanket to the reaction flask with constant stirring over 10 minutes. Another 350 grams of 1,2-dimethoxy ethane and lillial oxime (300 grams, source) in an Erlenmeyer flask. The lillial oxime solution was added to the reactor over three hours while monitoring hydrogen evolution with the bubbler. After all the NaH was finished reacting, methyl iodide (337 grams, Aldrich) was added over 3 hours. The reactor contents were cooled to −10° C. and 150 ml of water was added dropwise over 35 minutes. The contents were moved to a separatory funnel and washed with 500 ml of toluene and 500 ml of water. The organic phase was washed with 3-1000 ml water washes, one 1000 ml 2.5% acetic acid wash and two-1000 ml water washes. The remaining material was filtered through Celite and sodium sulfate and distilled: BP=128° C.

at 3.32 mmHg and 813 grams of crude product was recovered providing a yield of 44%.

NMR data 1.1 ppm (d,3H), 1.3 ppm (s,9H), 2.5–2.85 ppm (m, 3H), 3.8 ppm (s, 3H), 7.1–7.35 ppm (m, 5H).

The fragrance of this compound was evaluated and was described as muguet and floral notes.

EXAMPLE 13

Incorporation of an Oxime Methyl Ether in a Fragrance Formulation

The following fragrance was prepared using a compound of the present invention:

| INGREDIENTS | PARTS BY WEIGHT |
|---|---|
| Acetyl iso eugenol | 1.0 |
| 1,3-benzodioxole-5-carboxaldehyde,O-(2-methyl-2-propenyl) oxime | 40 |
| Canthoxal | 10 |
| Cinnamic alcohol (10% in DPG) | 10 |
| Dipropylene glycol | 417 |
| Ethyl vanillin (10% in DPG) | 2 |
| Heliotropine | 50 |
| Vanitrope (10% in DPG) | 50 |
| Veratrald | 120 |

The above fragrance was found to be a pleasing fragrance with pleasing green notes. The above fragrance formulation was presented to demonstrate the effectiveness of the compounds of the present invention was enhancing, improving or modifying the performance of the formulations in which they are incorporated.

What is claimed is:

1. A method for improving, enhancing or modifying a fragrance through the addition of an olfactory acceptable amount of the compound selected from the group consisting of:

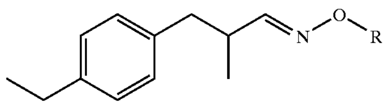

R=Me, Et, Allyl, Methylallyl, Cyclopentyl

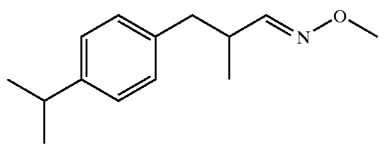

-continued

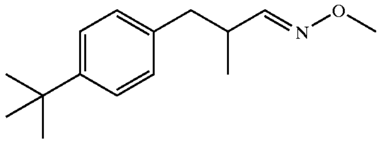

2. The method of claim 1 wherein the fragrance is incorporated into a product selected from perfumes, colognes, candles, toilet waters, cosmetic products, personal care products, fabric care products, cleaning products and air fresheners.

3. The method of claim 2 wherein the cleaning product is selected from the group consisting of soaps, detergents, dishwashing compositions, scrubbing compounds and window cleaners.

4. The method of claim 2 wherein the product is a personal care product.

5. The method of claim 1 wherein the level is from about 0.005 to about 10 weight percent.

6. The method of claim 1 wherein the level is from about 0.1 to about 8 weight percent.

7. The method of claim 1 wherein the level is from about 0.5 to about 5 weight percent.

8. The method of claim 1 wherein the R group in the compound is an alkyl moiety.

9. The method of claim 1 wherein the R group in the compound is an allyl moiety.

10. The method of claim 1 wherein the R group in the compound is cylcopentyl.

11. The method of claim 8 wherein the fragrance is incorporated into a product selected from perfumes, colognes, candles, toilet waters, cosmetic products, personal care products, fabric care products, cleaning products and air fresheners.

12. The method of claim 9 wherein the fragrance is incorporated into a product selected from perfumes, colognes, candles, toilet waters, cosmetic products, personal care products, fabric care products, cleaning products and air fresheners.

13. The method of claim 10 wherein the fragrance is incorporated into a product selected from perfumes, colognes, candles, toilet waters, cosmetic products, personal care products, fabric care products, cleaning products and air fresheners.

14. A compound having the structure set forth in claim 1.

15. A fragrance composition containing an olfactory effective amount of the compounds of claim 14.

* * * * *